(12) United States Patent
Hu et al.

(10) Patent No.: US 9,223,063 B2
(45) Date of Patent: Dec. 29, 2015

(54) SENSING METHOD AND SYSTEM FOR FRESNEL LENS

(75) Inventors: Xiaoping Hu, Guangdong (CN); Bin Tian, Guangdong (CH)

(73) Assignee: BOLY MEDIA COMMUNICATIONS (SHENZHEN) CO., LTD., Guangdong (CN)

( * ) Notice: Subject to any disclaimer, the term of this patent is extended or adjusted under 35 U.S.C. 154(b) by 61 days.

(21) Appl. No.: 13/978,350

(22) PCT Filed: Jul. 7, 2011

(86) PCT No.: PCT/CN2011/076949
§ 371 (c)(1),
(2), (4) Date: Jul. 31, 2013

(87) PCT Pub. No.: WO2012/092764
PCT Pub. Date: Jul. 12, 2012

(65) Prior Publication Data
US 2013/0308207 A1 Nov. 21, 2013

(30) Foreign Application Priority Data

Jan. 6, 2011 (CN) .......................... 2011 1 0002010

(51) Int. Cl.
*F21S 8/00* (2006.01)
*G02B 3/08* (2006.01)
(Continued)

(52) U.S. Cl.
CPC ................ *G02B 3/08* (2013.01); *G02B 3/0037* (2013.01); *G02B 3/0043* (2013.01);
(Continued)

(58) Field of Classification Search
CPC ......... G01J 1/0411; G01J 5/0896; G01J 5/54; G01N 21/84; G01N 15/0205; G02B 21/0032; G02B 19/0009; G02B 27/4272; G02B 5/1861; G02B 6/0051

USPC ......... 362/268; 356/4.09, 398, 602, 623, 954; 359/742; 250/338.1, 340, 341.8, 353, 250/342, 395, 237 R, 216, 227.2, 550, 250/559.16, 559.17, 559.29–559.49

See application file for complete search history.

(56) References Cited

U.S. PATENT DOCUMENTS

| | | | | |
|---|---|---|---|---|
| 4,321,594 A | * | 3/1982 | Galvin et al. | 250/342 |
| 4,769,545 A | * | 9/1988 | Fraden | 250/342 |
| 5,296,707 A | * | 3/1994 | Nozu | 250/342 |

FOREIGN PATENT DOCUMENTS

| | | |
|---|---|---|
| CN | 2879218 Y | 3/2007 |
| CN | 2898854 Y | 5/2007 |

(Continued)

OTHER PUBLICATIONS

International Search Report and Written Opinion for Application No. PCT/CN2011/076949, dated Oct. 20, 2011.

*Primary Examiner* — Evelyn A Lester
(74) *Attorney, Agent, or Firm* — Alston & Bird LLP (57) ABSTRACT

A sensing method and system for Fresnel lenses are disclosed, the system including a first Fresnel lens unit for sensing the signal of a target object crossing a first boundary of a sensing area, a second Fresnel lens unit for sensing the signal of a target object crossing a second boundary of the sensing area, a third Fresnel lens unit for sensing the signal of a target object crossing a third boundary of the sensing area, and a sensing unit for receiving and processing the sensed signals of the Fresnel lens units. The first and second Fresnel lens units are arranged on two sides of the third Fresnel lens unit. Furthermore, it is possible to add more Fresnel lens units above, below or around the Fresnel lens units. By monitoring the boundaries of the sensing area, the sensing method and system for the Fresnel lenses improve the insufficiency of the sensing area, reduce cost and save power consumption.

16 Claims, 6 Drawing Sheets

(51) Int. Cl.
*H01J 3/14* (2006.01)
*G02B 6/06* (2006.01)
*G01N 21/86* (2006.01)
*G02B 3/00* (2006.01)
G01J 1/04 (2006.01)
G01J 5/08 (2006.01)
F21V 8/00 (2006.01)
G02B 27/42 (2006.01)
G02B 5/18 (2006.01)
G01J 5/54 (2006.01)
G02B 19/00 (2006.01)
G01N 21/84 (2006.01)
G02B 21/00 (2006.01)

(52) U.S. Cl.
CPC ............ *G02B 3/0056* (2013.01); *G01J 1/0411* (2013.01); *G01J 5/0896* (2013.01); *G01J 5/54* (2013.01); *G01N 21/84* (2013.01); *G02B 5/1861* (2013.01); *G02B 6/0051* (2013.01); *G02B 19/0009* (2013.01); *G02B 21/0032* (2013.01); *G02B 27/4272* (2013.01)

(56) References Cited

FOREIGN PATENT DOCUMENTS

| | | |
|---|---|---|
| CN | 101315470 A | 3/2008 |
| CN | 201562333 U | 8/2010 |
| WO | WO-2008/132333 A1 | 11/2008 |

* cited by examiner

SENSING METHOD AND SYSTEM FOR FRESNEL LENS

FIELD OF THE INVENTION

The present invention relates to a Fresnel lens sensing method and system.

BACKGROUND OF THE INVENTION

Figure 1:
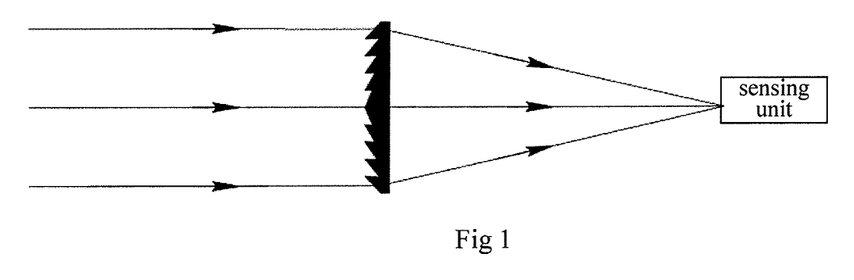
FIG. 1 is featured light path diagram of prior art Fresnel lens.
Figure 2:
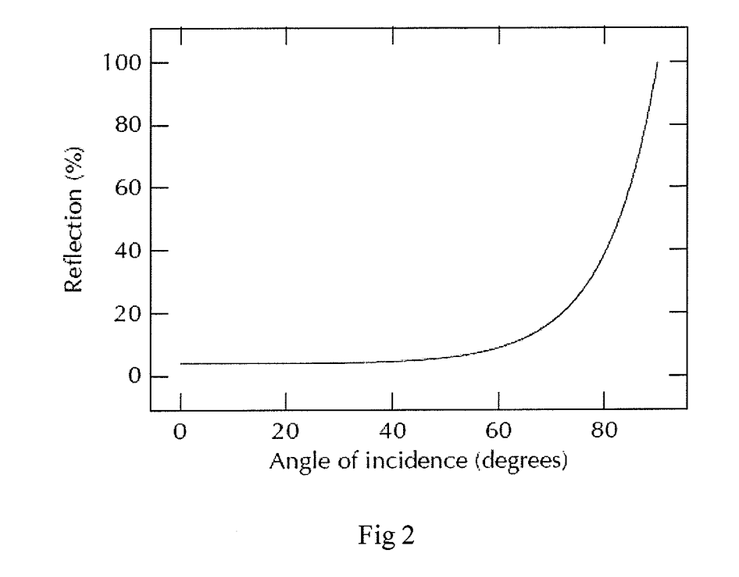
FIG. 2 is correlation diagram between incident angle and discrete incident angle of prior art Fresnel lens.
Figure 31:
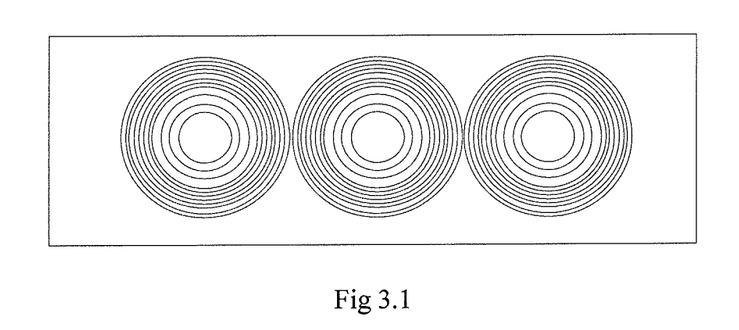
Figure 32:
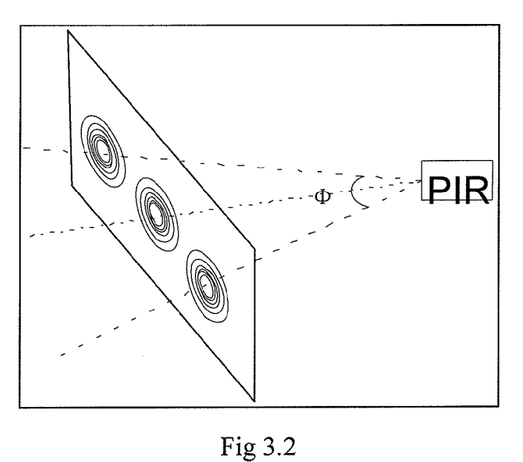
Figure 33:
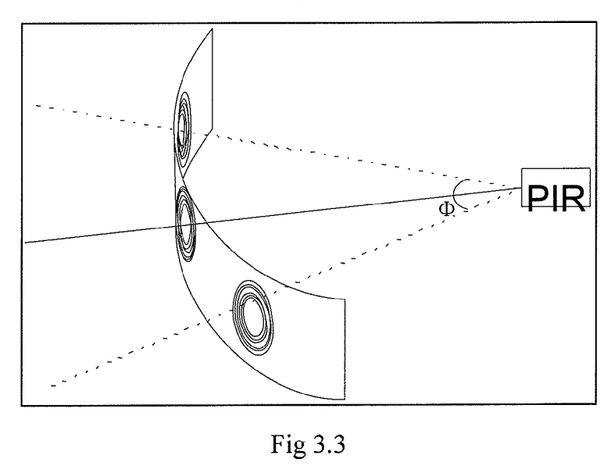
Figure 34:
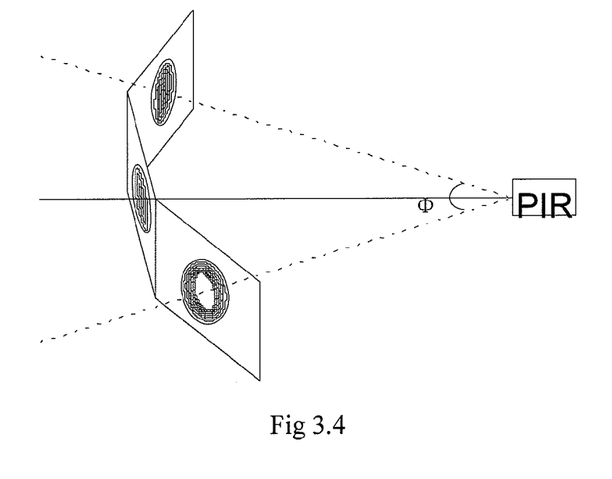
Figure 41:
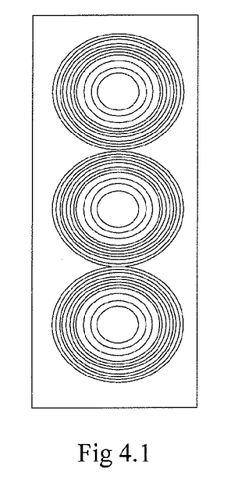
Figure 42:
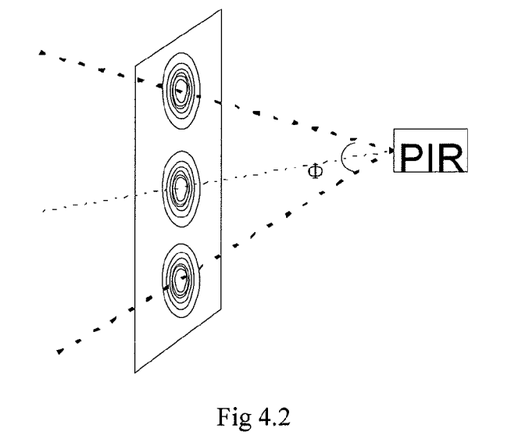
Figure 43:
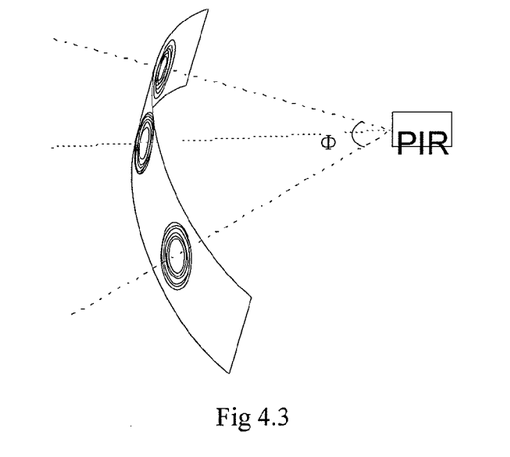
Figure 44:
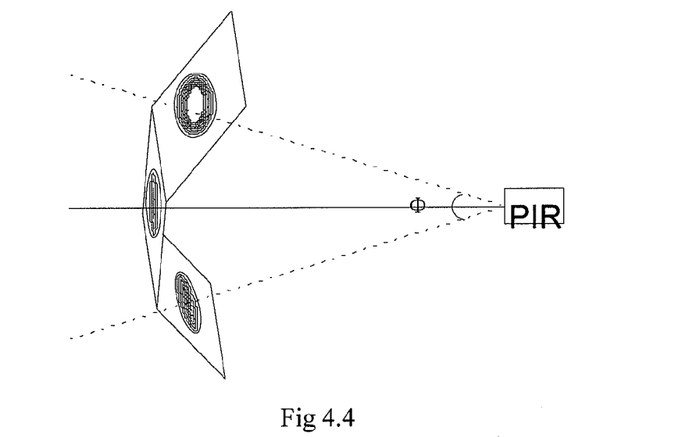
Figure 51:
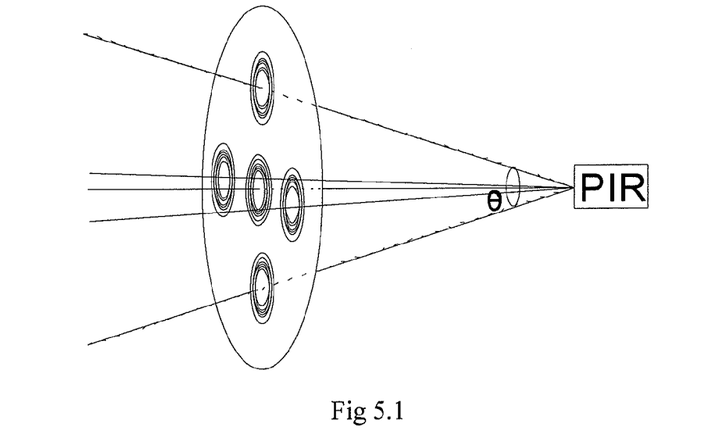
Figure 52:
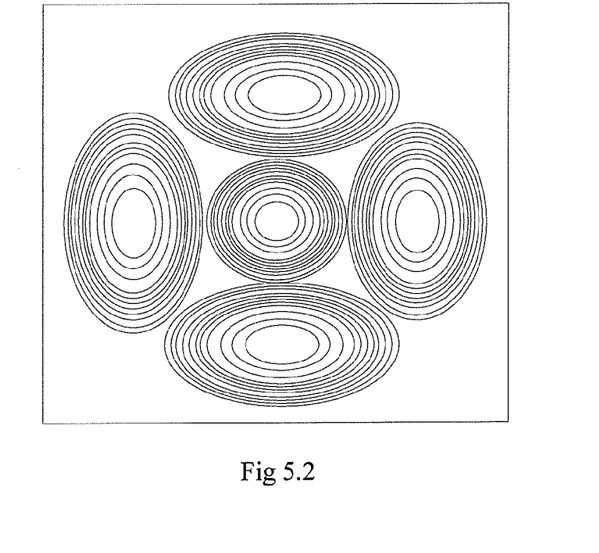
Figure 53:
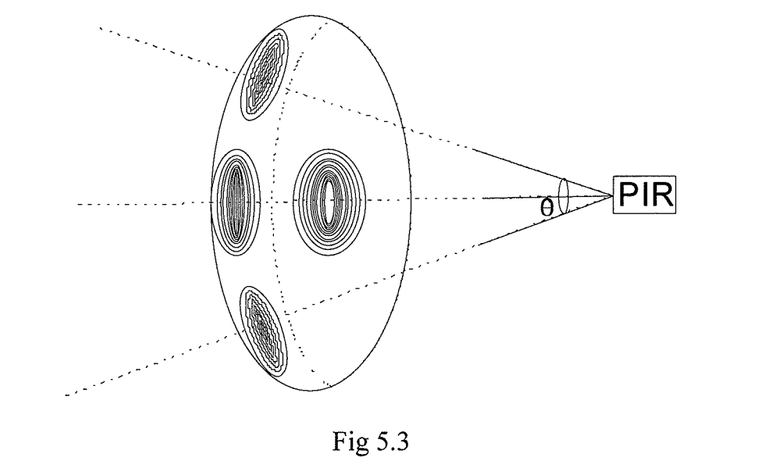
Figure 54:
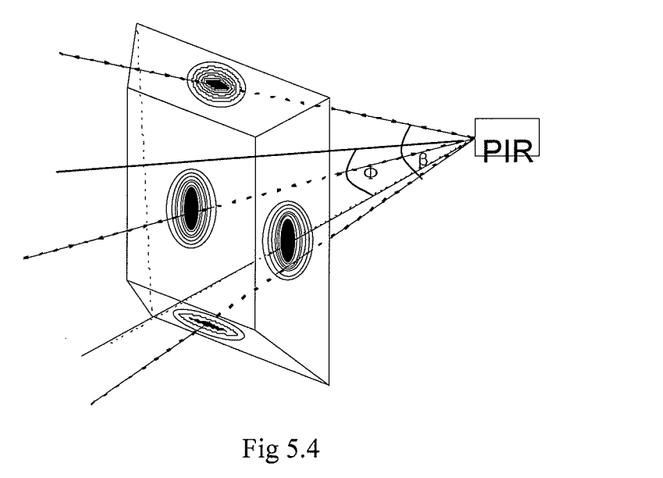
Figure 61:
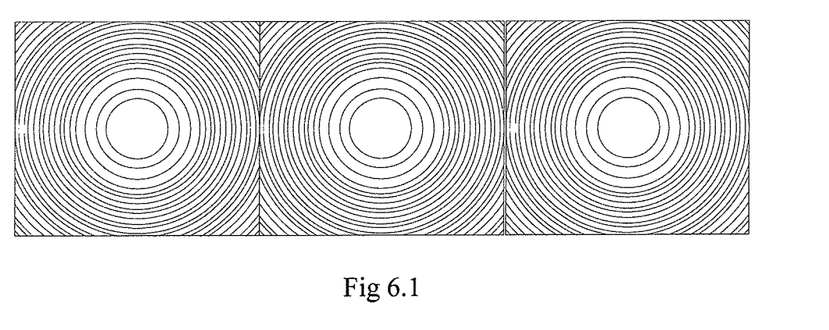
Figure 62:
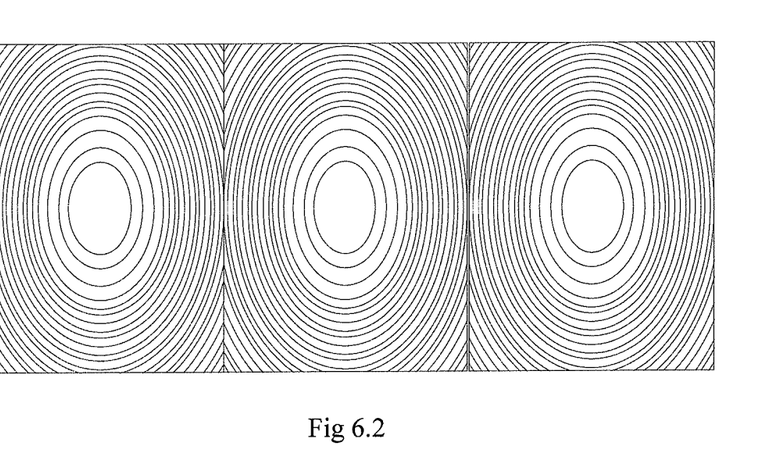
Figure 63:
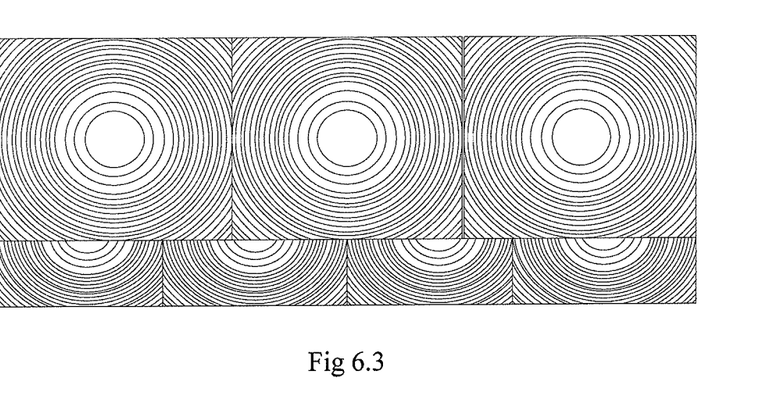

Fresnel lens sensing system combines Fresnel lens unit and sensing unit to form a signal sensing system, wherein the Fresnel lens sense optical signals, and the sensing unit receives signals and does signal processing. Refer to FIGS. 1 and 2, the surface of Fresnel lens generally consists of concentric jagged or stepped surface, the Fresnel lens sensing signal is characterized in: long central sensing distance, big signal strength, the sharp attenuation of the sensing distance and signal strength in surrounding area. The featured light path is as shown in FIG. 1. In FIG. 2, when incident discrete angle is bigger, the dispersion of the incident signals is larger, the attenuation of the intensity is larger.

An application in monitoring system of the Fresnel lens is used to start the imaging system of the monitoring system, making the imaging system to start videoing and photographing only when the object motion is detected, resulting in reducing data amount and decreasing the power consumption of the system.

The Fresnel lens sensing system is mainly used in inspection and monitoring field, classified in two types, one type is generally to dispose a Fresnel lens unit to detect a narrow area, such as human body detection of automatic toilet, which requires the detection area to be focused on the narrow area short distance away from the front side of automatic toilet, avoiding mis-flushing operation due to mis-detection; the other type is to detect warm-blooded creatures in a certain area, the conventional design ideas of this kind of application is based on the design ideas of no blind area monitoring, which is designed to inspect every point or sub-area of the inspected area, this kind of no blind area design is realized by densely disposing a plurality of Fresnel lens units. However, the drawbacks of this dense disposition are: 1) the dense disposition may incur the area reduction of each Fresnel lens, resulting in short monitoring distance; 2) the dense disposition of Fresnel lens may incur over-sensing with very slight motion in the area, resulting in frequent photographing, the two photos in very short interval may be the same regarding the monitoring information, which actually is unnecessary and waste of resources.

SUMMARY OF THE INVENTION

In view of the above background, the present invention provides a Fresnel lens sensing method and system to improve the drawbacks of detection range of the current Fresnel lens sensing system.

In order to solve the above technical issues, the present invention uses the following technical solutions:

A Fresnel lens sensing method, consisting of:

Predetermined sensing area, the sensing area having a first boundary, a second boundary and a third boundary;

At least sensing signals of targets crossing the first boundary via a first Fresnel lens unit;

At least sensing signals of targets crossing the second boundary via a second Fresnel lens unit;

At least sensing signals of targets crossing the third boundary via a third Fresnel lens unit;

Receiving and processing the signals sensed by the Fresnel lens units via sensing unit.

In the above Fresnel lens sensing method, the first boundary is left boundary, the second boundary is right boundary, the third boundary is frontal boundary.

Another Fresnel lens sensing method provided by the present invention, consisting of:

Predetermined sensing area, the sensing area having a first boundary, a second boundary, a third boundary and a fourth boundary;

At least sensing signals of targets crossing the first boundary via a first Fresnel lens unit;

At least sensing signals of targets crossing the second boundary via a second Fresnel lens unit;

At least sensing signals of targets crossing the third boundary via a third Fresnel lens unit;

At least sensing signals of targets crossing the fourth boundary via a fourth Fresnel lens unit;

Receiving and processing the signals sensed by the Fresnel lens units via sensing unit.

In the above Fresnel lens sensing method, the first boundary is left side, the second boundary is right side, the third boundary is front side, the fourth boundary is upper side or lower side close to ground.

Still another Fresnel lens sensing method provided by the present invention, consisting of:

Predetermined sensing area, the sensing area having a first boundary, a second boundary, a third boundary, a fourth boundary and a fifth boundary;

At least sensing signals of targets crossing the first boundary via a first Fresnel lens unit;

At least sensing signals of targets crossing the second boundary via a second Fresnel lens unit;

At least sensing signals of targets crossing the third boundary via a third Fresnel lens unit;

At least sensing signals of targets crossing the fourth boundary via a fourth Fresnel lens unit;

At least sensing signals of targets crossing the fifth boundary via a fifth Fresnel lens unit;

Receiving and processing the signals sensed by the Fresnel lens units via sensing unit.

In the above Fresnel lens sensing method, the first boundary is left side, the second boundary is right side, the third boundary is front side, the fourth boundary is upper side, the fifth boundary is lower side close to ground.

A Fresnel lens sensing system provided by the present invention consists of a first Fresnel lens unit used to sense signals of targets crossing a first boundary of sensing area, a second Fresnel lens unit used to sense signals of targets crossing a second boundary of sensing area, a third Fresnel lens unit used to sense signals of targets crossing a third boundary of sensing area, a sensing unit used to receive and process the sensing signals of the Fresnel lens units, the first and second Fresnel lens unit are disposed on the two sides of the third Fresnel lens unit respectively.

In the Fresnel lens sensing system, the first, second and third Fresnel lens units are disposed on a plane, or disposed on three planes which are formed by folding a plane; or the first, second and third Fresnel lens units are disposed on a cylindrical surface, elliptic cylinder surface, parabolic cylinder surface, or quadric cylinder surface which are of hyperbolic cylinder surface.

Another Fresnel lens sensing system provided by the present invention consists of a first Fresnel lens unit used to sense signals of targets crossing a first boundary of sensing area, a second Fresnel lens unit used to sense signals of targets crossing a second boundary of sensing area, a third Fresnel lens unit used to sense signals of targets crossing a third boundary of sensing area, a fourth Fresnel lens unit used to sense signals of targets crossing a fourth boundary of sensing area, and a sensing unit used to receive and process the sensing signals of the Fresnel lens units.

In the Fresnel lens sensing system, the fourth boundary is the lower side close to ground.

In the Fresnel lens sensing system, the first, second, third and fourth Fresnel lens units are disposed on a plane, or disposed on the four planes of a ladder platform; or the first, second, third and fourth Fresnel lens units are disposed on a sphere surface, ellipsoid surface, paraboloid surface, or quadric surface which are of hyperboloid surface.

Still another Fresnel lens sensing system provided by the present invention consists of a first Fresnel lens unit used to sense signals of targets crossing a first boundary of sensing area, a second Fresnel lens unit used to sense signals of targets crossing a second boundary of sensing area, a third Fresnel lens unit used to sense signals of targets crossing a third boundary of sensing area, a fourth Fresnel lens unit used to sense signals of targets crossing a fourth boundary of sensing area a sensing unit used to receive, a fifth Fresnel lens unit used to sense signals of targets crossing a fifth boundary of sensing area, and a sensing unit used to receive and process the sensing signals of the Fresnel lens units. The first, second, third and fourth Fresnel lens units are distributed symmetrically with the symmetry center of the fifth Fresnel lens unit.

In the Fresnel lens sensing system, the first, second, third, fourth and fifth Fresnel lens units are disposed on a plane, or disposed on the five planes of a ladder platform; or the first, second, third, fourth and fifth Fresnel lens units are disposed on a sphere surface, ellipsoid surface, paraboloid surface, or quadric surface which are of hyperboloid surface.

The Fresnel lens sensing system disclosed by the present invention has one sensing unit, on which each Fresnel lens focuses, has a plurality of sensing units, each sensing unit has a correspondence Fresnel lens unit.

In the Fresnel lens sensing system disclosed by the present invention, the sensing unit is infrared sensing detection unit (PIR: Passive Infrared Detection).

In the Fresnel lens sensing system disclosed by the present invention, the sensing angle of the sensing area is substantially equal to the angle of FOV.

In the Fresnel lens sensing system disclosed by the present invention, the surface of the Fresnel lens unit is carved into jagged or stepped surface of concentric circles, concentric ellipses or concentric polygons.

The advantageous effects of the present invention are:

(1) The present invention abandons the conventional idea of dense area points monitoring, uses boundary monitoring approach, that is, when in monitoring, it is mainly to sense the scenario of the monitored objects crossing the boundary of the monitored area, for the design of applying the first, second and third Fresnel lens unit, each Fresnel lens unit is responsible for signals of targets crossing the first, second or third boundary of the sensing area respectively, for example, the first boundary is the left boundary of the sensing area, the second boundary is the right boundary of the sensing area, and the third boundary is the front boundary of the sensing area; Taking the animal monitoring for example, because the animals must pass through the boundary of the monitoring range if they enter or leave the monitoring range, via the design, the Fresnel lens units are responsible for the monitoring of the boundaries of the sensing area, good monitoring effects could be achieved. Moreover, the photographing number could be greatly reduced due to the limit of the Fresnel lens units, so the energy could be focused on the most effective monitoring area, thus the power consumption could be saved with the increase of standing by time. While the first, second, third, fourth and fifty Fresnel lens units are designed, five boundaries could be monitored, i.e., the first boundary is the left side, the second boundary is the right side, the third boundary is the front side, the fourth boundary is the upper side, the fifth boundary is the lower side close to the ground, therefore the monitoring area could be expanded three-dimensionally. As a simplification, only the first, second, third and fourth Fresnel lens units are designed, that is to remove a Fresnel lens unit.

As a more practical optimization of the present invention, besides the first, second, third, fourth and fifth Fresnel lens units, extra Fresnel lens units with smaller size could be added under or around the above five Fresnel lens units, used to cover the scenarios of entering or leaving the monitoring area from ground, sky or back of the sensing system to reach the goal of full coverage.

(2) Comparing with the prior art, on the one hand, the processing is simplified and processing cost is reduced due to the number reduction of the Fresnel lens units in the same area; on the other hand, with the identical overall size of the lens, the fewer the number of the Fresnel lens unit, the farther the sensing distance, due to the positive correlation between the sensing distance of the Fresnel lens and the surface area of the Fresnel lens. In the Fresnel sensing system disclosed by the present invention, the number of the main Fresnel lens is reduced to 3-5, the area of each Fresnel lens is larger than one of the prior art, thus the sensing distance of the Fresnel lens unit could be increased, resulting in wider detection range, smaller size of the detection apparatus.

(3) The plurality of the Fresnel lens units are disposed on curved surfaces such as cambered surfaces, folded surfaces, on the one hand, facilitating more simplification of processing, on the other hand, making the shape of the whole monitoring range to be regular and avoiding to form irregular shape of the extrusive center.

The present invention uses most optimized 3-5 Fresnel lens units design or the design taking 3-5 Fresnel lens units as main body, reducing costs while still being able to ensure monitoring effect.

BRIEF DESCRIPTION OF THE DRAWINGS

FIG. 3 is a diagram of a Fresnel lens sensing system according to one embodiment of the present invention; wherein the angle $\Phi$ is formed by the central lines of the outside two lens unit, determined by the monitoring area of interest at the time of designing.

FIG. 4 is a diagram of a Fresnel lens sensing system according to another embodiment of the present invention; which actually depicts that the system as shown in FIG. 3 is rotated for 90 degree, it is intended to be a general example to describe simple modification of the system as shown in FIG. 3;

FIG. 5 is a diagram of a Fresnel lens sensing system according to still another embodiment of the present invention; which is finer expansion of the system as shown in FIG. 3; wherein the horizontal intersection angle and vertical intersection angle $\Phi$ and $\beta$ respectively, or cone angle $\Theta$, stand for sensing area of interest;

FIG. 6 is a simple expansion of FIG. 3 in practical use, which is intended to describe that simple modification and expansion are still within the protection scope of the present invention; the similar modification is also adapted to the Fresnel lens sensing system as shown in FIG. 5. FIG. 6.1 illustrates a Fresnel lens system design with the spiral fully filled on the whole lens surface; FIG. 6.2 is a modification from conventional concentric circle Fresnel lens unit to concentric elliptic Fresnel lens unit; FIG. 6.3 is a modification in which one Fresnel lens boundary sensing unit is realized by small and dense Fresnel lens units, used to cover the object entering and leaving from ground, sky or back of sensing system.

DETAILED DESCRIPTION OF THE INVENTION

Hereafter is the detailed description of the present invention according to the drawings combined with the embodiments.

The present invention is mainly based on the characteristics that the signals of central incident angle of Fresnel lens are strong while the signals of edging incident angle are weak, fully using the stronger central signals to detect the borderline of monitoring area, unlike the prior art that monitors the inside points of monitoring area, therefore the goals of expanding the detection range and reducing the power consumption and lens size could be achieved, and reducing repetitive data amount significantly as well.

A Fresnel lens sensing system according to an embodiment of the present invention consists of a first Fresnel lens unit used to sense signals of targets crossing a first boundary of sensing area, a second Fresnel lens unit used to sense signals of targets crossing a second boundary of sensing area, a third Fresnel lens unit used to sense signals of targets crossing a third boundary of sensing area, a sensing unit used to receive and process the sensing signals of the Fresnel lens units, the first and second Fresnel lens unit are disposed at the two sides of the third Fresnel lens unit respectively. Wherein the first boundary is the left boundary of the sensing area, the second boundary is the right boundary, and the third boundary is the front boundary.

In another embodiment, a Fresnel lens sensing system of the present invention consists of a first Fresnel lens unit used to sense signals of targets crossing a first boundary of sensing area, a second Fresnel lens unit used to sense signals of targets crossing a second boundary of sensing area, a third Fresnel lens unit used to sense signals of targets crossing a third boundary of sensing area, a fourth Fresnel lens unit used to sense signals of targets crossing a fourth boundary of sensing area a sensing unit used to receive and process the sensing signals of the Fresnel lens units. Wherein the first boundary is the left side of the sensing area, the second boundary is the right side of the sensing area, and the third boundary is the front side of the sensing area, the fourth boundary is the upper side of the sensing area or the lower side of the sensing area close to ground.

In still another embodiment, the Fresnel lens sensing system of the present invention consists of a first Fresnel lens unit used to sense signals of targets crossing a first boundary of sensing area, a second Fresnel lens unit used to sense signals of targets crossing a second boundary of sensing area, a third Fresnel lens unit used to sense signals of targets crossing a third boundary of sensing area, a fourth Fresnel lens unit used to sense signals of targets crossing a fourth boundary of sensing area a sensing unit used to receive, a fifth Fresnel lens unit used to sense signals of targets crossing a fifth boundary of sensing area a sensing unit used to receive and process the sensing signals of the Fresnel lens units. The first, second, third and fourth Fresnel lens units are distributed symmetrically with the symmetry center of the fifth Fresnel lens unit. Wherein the first boundary is the left side of the sensing area, the second boundary is the right side of the sensing area, and the third boundary is the front side of the sensing area, the fourth boundary is the upper side of the sensing area, and the fifth boundary is the lower side of the sensing area close to ground.

The Fresnel lens units could be disposed on a plane, and the surrounding Fresnel lens units are disposed on the two sides or all-around of the central Fresnel lens unit, generally could be disposed equaldistantly; or the Fresnel lens units could be disposed on a curved surface which has the same radius of curvature to a central point, in like manner, the surrounding Fresnel lens units could be also disposed on the two sides or all-around of the central Fresnel lens unit equaldistantly. The curved surface could be cambered surface or folded surface, etc.

A plurality of sensing units could be configured, so that one sensing unit has correspondence Fresnel lens unit. Or one sensing unit is configured, each Fresnel lens unit focuses on the sensing unit.

The sensing unit could be infrared detection unit (PIR) for example. Hereafter takes PIR as sensing unit to describe, the skill in the art should understand that other types of sensing units may be applicable to the sensing system of the present invention.

FIG. 3 and FIG. 4 illustrate 3 Fresnel lens units' design, it can be seen that those Fresnel lens units could be disposed on a plane, or three planes folded by one plane, or one quadric cylinder surface (cylinder surface, elliptic cylinder surface, parabolic cylinder surface, or hyperbolic cylinder surface). For example, FIG. 3.1 illustrates horizontally disposed 3 Fresnel lens units, in horizontal direction different arrangement structure could be formed as shown in FIG. 3.2 (3 Fresnel lens units are on one plane), or FIG. 3.3 (3 Fresnel lens units are on cambered surface), or FIG. 3.4 (3 Fresnel lens units are on 3 planes folded by one plane), the 3 Fresnel lens units could form a monitoring area with wide range and long distance (i.e. 120°×25 M) in horizontal direction, that is, the sensing angle of the sensing area could be 120 degree, and sensing distance could be 25 meters, while Fresnel lens sensing system in prior art generally only covers area of 120°×6 M or 50°×9 M.

FIG. 4 illustrates simple modifications in monitoring direction or mounting direction of the Fresnel lens sensing system as shown in FIG. 3.

FIG. 5 illustrates 5 Fresnel lens units' design, it can be seen that those Fresnel lens units could be disposed on a plane, or five planes folded by one plane, or one quadric surface (sphere surface, ellipsoid, paraboloid, or hyperboloid). Refer to the example in FIG. 5, FIGS. 5.1 and 5.2 illustrates that one of the 5 Fresnel lens units is centered, the other four are disposed around the central one and distributed symmetrically to the central Fresnel lens unit, that is, the system includes a central Fresnel lens unit, two Fresnel lens units disposed in horizontal direction on left and right side of the central Fresnel lens unit, and two Fresnel lens units disposed in vertical direction on upper and lower side of the central Fresnel lens unit. In the example of FIG. 5.3, the cambered surface could further form a quadric surface of semi-sphere surface, ellipsoid, paraboloid, or hyperboloid; in the example of FIG. 5.4, the folded plane could further form ladder platform, the 5 Fresnel lens units are disposed on the top surface and 4 side surfaces of the ladder platform, making PIR have long detection distance and no detection dead space in each direction and detection angle at the same time. Accordingly, the distribution of the plurality of Fresnel lens units is very flexible with different detection location according to predetermined configuration, each Fresnel lens unit could be used independently in its position or direction.

As shown in FIGS. 3, 4 and 5, points detection is changed to boundary detection through changing the detection focus of Fresnel lens, it is to use the characteristics of strong signals at the center and great signal attenuation on the side of the Fresnel lens to expand monitoing area, reduce system power consumption, decrease system size and reduce repetitive information as well. Fresnel lens system may be circular or rectangular, the Fresnel lens units may be concentric circles, concentric ellipses (as shown in FIG. 6.2), or concentric polygons (only simple modification from circles to polygons, not shown).

Obviously, the above embodiments are only simple examples of present invention. The professionals familiar with Fresnel sensing system and infrared detection could benefit from the advantages brought by present invention easily with many simple modifications according to the spirits of present invention.

FIG. 6.1 is an embodiment of FIG. 3.1 and FIG. 4.1. FIG. 6.2 is an embodiment of FIGS. 3.1 and 4.1 which uses concentric ellipses Fresnel lens units. FIG. 6.3 is an embodiment which takes FIG. 3.1 and FIG. 4.1 (3 Fresnel lens unit systems) as main body with some minor modifications to the sides. It can be seen that the fourth boundary of monitoring area is disposed under the first, second and third Fresnel lens units, i.e., the lower side close to ground is set to the fourth boundary. The four fourth Fresnel lens units corresponding to the fourth boundary are used to sense the signals of targets crossing the fourth boundary, thus the fourth boundary that is the monitoring area of the lower side close to ground is expanded. Meanwhile, Fresnel lens size of each of the fourth Fresnel lens units is smaller than one of each of the first, second and third Fresnel lens units. If the first, second and third Fresnel lens units are named the first group Fresnel lens unit, the fourth Fresnel lens units are named the second group Fresnel lens unit, the density of the second group Fresnel lens unit is bigger than one of the first group Fresnel lens unit, because the size of Fresnel lens units of the second group Fresnel lens unit is smaller than one of the first group Fresnel lens unit, on the same lens area, the number of Fresnel lens units of the second group Fresnel lens units is much more than one of the first group Fresnel lens units. The purpose of setting the second group Fresnel lens unit is to cover the entering and leaving situation of the objects of ground and backside of the sensing system. Obviously, the simple modification could be used in 5 Fresnel lens units system. If one of the 5 Fresnel lens units system is not used, the system could be easily retrogressed to 4 Fresnel lens units system. Either the central Fresnel lens unit or one of the Fresnel lens units on the side could be moved. The simple modification is of course within the scope of present invention. Similarly, the first, second and third Fresnel lens units could use plurality of Fresnel lens units respectively to expand the monitoring area of the first, second and third boundary.

As a part of the whole monitoring system, Fresnel lens sensing system is used in conjunction with imaging system, i.e. once the Fresnel lens sensing system detects an object, the imaging system is started to take photograph. Accordingly, the sensing angle of the sensing area of the Fresnel lens sensing system is substantially equal to the angle of FOV of the imaging system to ensure the starting precision of photographing and avoid accidental photographing and missing photographing.

The present invention could reinforce the magnification of detection signals in the direction of horizontal, vertical and full hemisphere, increase the detection range and distance of the Fresnel lens and infrared sensing system, expand the detection range of the whole system, and improve the performance of the whole detection system, therefore multi-direction, multi-point, multi-target and large range detection system or security detection system could be achieved.

The above is the detailed description to the present invention in conjunction with specific embodiments, it is not to be understood that the embodiments of the present invention are limited to this description. For the skill in the art, without departing from the idea of the present invention, plurality of simple deductions and replacements could be made which should be regarded as belonging to the protection scope of the present invention.

The invention claimed is:

1. A Fresnel lens sensing method, comprising:
a predetermined sensing area comprising a first boundary, a second boundary, and a third boundary;
at least sensing signals of targets crossing the first boundary via a first Fresnel lens unit;
at least sensing signals of targets crossing the second boundary via a second Fresnel lens unit;
at least sensing signals of targets crossing the third boundary via a third Fresnel lens unit; and
receiving and processing the signals sensed by the Fresnel lens units via a sensing unit;
wherein the first, second, and third boundaries are borderlines of the sensing area, and wherein the borderlines are detected by central signals of the first, second, and third Fresnel lens units, accordingly.

2. The method of claim 1, wherein the first boundary is a left boundary, the second boundary is a right boundary, and the third boundary is a frontal boundary.

3. The method of claim 1, the sensing area further having a fourth boundary, the method further comprising:
at least sensing signals of targets crossing the fourth boundary via a fourth Fresnel lens unit.

4. The method of claim 3, wherein the first boundary is a left side, the second boundary is a right side, the third boundary is a front side, the fourth boundary is an upper side or a lower side close to ground.

5. The method of claim 3, the sensing area further having a fifth boundary, the method further comprising:
at least sensing signals of targets crossing the fifth boundary via a fifth Fresnel lens unit.

6. The method of claim 5, wherein the first boundary is a left side, the second boundary is a right side, the third boundary is a front side, the fourth boundary is an upper side, the fifth boundary is a lower side close to ground.

7. A Fresnel lens sensing system, comprising a first Fresnel lens unit used to sense signals of targets crossing a first boundary of sensing area, a second Fresnel lens unit used to sense signals of targets crossing a second boundary of sensing area, a third Fresnel lens unit used to sense signals of targets crossing a third boundary of sensing area, a sensing unit used to receive and process the sensing signals of the Fresnel lens units, the first and second Fresnel lens unit are disposed on the two sides of the third Fresnel lens unit respectively; wherein the first, second, and third boundaries are borderlines of the sensing area, and wherein the borderlines are detected by central signals of the first, second, and third Fresnel lens units, accordingly.

8. The system in claim 7, wherein the first, second and third Fresnel lens units are disposed on a plane, or disposed on three planes which are formed by folding a plane; or the first, second and third Fresnel lens units are disposed on a cylindrical surface, elliptic cylinder surface, parabolic cylinder surface, or quadric cylinder surface which are of hyperbolic cylinder surface.

9. The system of claim 7, comprising one sensing unit, on which each Fresnel lens focuses, and a plurality of sensing units, each sensing unit has a correspondence Fresnel lens unit.

10. The system of claim 7, wherein the sensing unit is an infrared sensing detection unit (PIR).

11. The system of claim 7, wherein the surface of the Fresnel lens unit is carved into jagged or stepped surface of concentric circles, concentric ellipses or concentric polygons.

12. A Fresnel lens sensing system, comprising a first Fresnel lens unit used to sense signals of targets crossing a first boundary of sensing area, a second Fresnel lens unit used to sense signals of targets crossing a second boundary of sensing area, a third Fresnel lens unit used to sense signals of targets crossing a third boundary of sensing area, a fourth Fresnel lens unit used to sense signals of targets crossing a fourth boundary of sensing area, and a sensing unit used to receive and process the sensing signals of the Fresnel lens units; wherein the first, second, third, and fourth boundaries are borderlines of the sensing area, and wherein the borderlines are detected by central signals of the first, second, third, and fourth Fresnel lens units, accordingly.

13. The system of claim 12, wherein the fourth boundary is a lower side close to ground.

14. The system of claim 12, wherein the first, second, third and fourth Fresnel lens units are disposed on a plane, or disposed on four planes of a ladder platform; or the first, second, third and fourth Fresnel lens units are disposed on a sphere surface, ellipsoid surface, paraboloid surface, or quadric surface which are of hyperboloid surface.

15. The system of claim 12, further comprising a fifth Fresnel lens unit used to sense signals of targets crossing a fifth boundary of sensing area, the first, second, third and fourth Fresnel lens units are distributed symmetrically with the symmetry center of the fifth Fresnel lens unit.

16. The system of claim 15, wherein the first, second, third, fourth and fifth Fresnel lens units are disposed on a plane, or disposed on five planes of a ladder platform;
or the first, second, third, fourth and fifth Fresnel lens units are disposed on a sphere surface, ellipsoid surface, paraboloid surface, or quadric surface which are of hyperboloid surface.

\* \* \* \* \*